United States Patent
Kokozidis

(10) Patent No.: US 12,390,946 B2
(45) Date of Patent: Aug. 19, 2025

(54) RAZOR HEAD

(71) Applicant: BIC Violex Single Member S.A., Anoixi (GR)

(72) Inventor: Michail Kokozidis, Anoixi (GR)

(73) Assignee: BIC Violex Single Member S.A., Anoixi (GR)

( * ) Notice: Subject to any disclaimer, the term of this patent is extended or adjusted under 35 U.S.C. 154(b) by 195 days.

(21) Appl. No.: 18/485,102

(22) Filed: Oct. 11, 2023

(65) Prior Publication Data
US 2024/0123639 A1  Apr. 18, 2024

(30) Foreign Application Priority Data

Oct. 12, 2022 (EP) ..................................... 22201177

(51) Int. Cl.
*B26B 21/22* (2006.01)
*B26B 21/34* (2006.01)

(52) U.S. Cl.
CPC ............ *B26B 21/222* (2013.01); *B26B 21/34* (2013.01)

(58) Field of Classification Search
CPC ................................ B26B 21/22; B26B 21/34
See application file for complete search history.

(56) References Cited

U.S. PATENT DOCUMENTS

| | | | |
|---|---|---|---|
| 4,754,547 A | 7/1988 | Butka | |
| 5,022,154 A * | 6/1991 | Johnson | B26B 19/18 30/34.2 |
| 5,678,311 A * | 10/1997 | Avidor | B26B 21/34 30/34.2 |
| 6,678,957 B2 * | 1/2004 | Floessholzer | B26B 19/04 30/34.2 |
| 7,953,610 B2 | 5/2011 | Rosow et al. | |
| 10,093,031 B2 * | 10/2018 | Ren | B26B 21/34 |
| 11,826,923 B2 * | 11/2023 | Kopelas | B26B 21/34 |
| 2005/0198826 A1 * | 9/2005 | Segrea | B26B 21/44 30/41 |
| 2015/0065950 A1 | 3/2015 | Banar | |
| 2015/0231382 A1 | 8/2015 | Altarac | |
| 2016/0207210 A1 * | 7/2016 | Ren | B26B 21/222 |
| 2021/0162682 A1 * | 6/2021 | Speaker | C08L 5/00 |

FOREIGN PATENT DOCUMENTS

| | | |
|---|---|---|
| EP | 1252985 A2 | 10/2002 |
| EP | 3922297 A2 | 12/2021 |
| WO | 9738830 A2 | 10/1997 |

OTHER PUBLICATIONS

Search Report issued in European Application No. 22201177.7, mailed Mar. 23, 2023.

\* cited by examiner

*Primary Examiner* — Omar Flores Sanchez
(74) *Attorney, Agent, or Firm* — Bookoff McAndrews, PLLC

(57) ABSTRACT

The present disclosure concerns a razor head comprising one or more shaving blades and a roller. The roller is adjacent to the shaving blades and includes a plurality of microneedles. A method for skin treatment using this razor head includes a microneedling step with the roller, wherein the microneedles penetrate under the stratum corneum.

15 Claims, 5 Drawing Sheets

RAZOR HEAD

This application claims priority from the European patent application EP22201177.7, filed on Oct. 12, 2022, the entire content of which being incorporated herein by reference.

TECHNICAL FIELD

The disclosure relates to a razor head and a method for cosmetic skin treatment using such a razor head.

BACKGROUND

The human epidermis comprises several layers, from the stratum basale adjacent to the dermis and rich in free nerve endings, to the stratum corneum, formed by dead keratinocytes and providing a barrier against abrasion, pathogens, light and heat. Microneedling devices and methods have been proposed by which very fine needles, with tip diameters in the micrometer range, penetrate under the stratum corneum without reaching the nerve endings in the stratum basale and dermis, to painlessly stimulate blood flow and skin regeneration. Hollow microneedles have also been proposed for delivering cosmetic, prophylactic and therapeutic agents under the stratum corneum. It has also been proposed to integrate the microneedles into patches or rollers to facilitate their use.

Separately, it has been proposed to incorporate rollers into razor heads to minimize friction during shaving, as in U.S. Pat. No. 7,953,610, and/or to deposit an agent, such as soap or lubricant, on the surface of the skin before the shaving blades, as in European patent application publication EP 1 252 985 A2.

SUMMARY

A first object of the disclosure is that of providing a razor head with a supplemental cosmetic and/or therapeutic function having a synergistic effect with its primary shaving function.

According to a first aspect of the disclosure, the razor head may comprise, besides one or more shaving blades, a roller which is adjacent to the shaving blades and includes a plurality of microneedles. The microneedles may have a length below 1.5 mm, more specifically below 1 mm, most specifically between 0.25 and 0.5 mm, and/or a tip thickness below 100 μm, more specifically below 50 μm, most specifically between 1 and 25 μm. The microneedles may be distributed over an outer surface of the roller with a surface density below 100 microneedles/mm$^2$, more specifically below 50 microneedles/mm$^2$, most specifically below 20 microneedles/mm$^2$. This distribution may be homogeneous over the outer surface of the roller. In examples, however, the distribution may be heterogeneous, for example following a density gradient and/or distribution pattern.

Consequently, concurrently to shaving, the microneedles may penetrate under the stratum corneum of the freshly shaven skin to stimulate blood flow and skin regeneration. With thusly reduced interference by body hairs, microneedling gains effectiveness. At the same time, microneedling will be performed with at least the same frequency as shaving, ensuring its regularity and periodicity for even greater effectiveness.

According to a second aspect of the disclosure, the microneedles may be hollow. Such hollow microneedles may be configured for delivery of a drug or skin care agent such as, for example, a sun care, hydrating, antioxidant and/or hair loss treatment agent, or for drawing fluid or tissue samples. The drug or skin care agent may for example comprise methylene blue as an eco-friendly sun care agent protecting against UV rays, while also repairing UV induced damage, moringa oleifera seed oil as a hydrating and antioxidant agent, and/or a mixture of hyaluronic acid and cerium-containing nanoparticles as an agent against hair loss. The roller may include an internal reservoir, in fluid communication with the hollow microneedles, and eventually also a sealable opening for refilling and/or emptying the internal reservoir, which may contain the drug, skin care agent, fluid samples or tissue samples.

Through the delivery of the drug or skin care agent under the stratum corneum, the razor head may perform an even more effective cosmetic and/or therapeutic treatment. Body fluid and tissue samples drawn from below the stratum corneum may also provide valuable insights for diagnostic.

According to a third aspect of the disclosure, a rotation axis of the roller may be substantially parallel to cutting edges of the shaving blades, to minimize friction in the shaving direction. Complementarily or alternatively to this, the rotation axis of the roller may be adjustable along another axis substantially orthogonal to a shaving plane to adjust the penetration depth of the microneedles under the skin surface. The roller may be substantially cylindrical to ensure a uniform penetration depth of the microneedles across its width in the direction of the rotation axis, and it may have a length, in the direction of the rotation axis, at least equal to a length of the cutting edges of the shaving blades, in order to treat the entire shaven surface of the skin.

According to a fourth aspect of the disclosure, the razor head may comprise a releasable cartridge containing the razor blades, so that the microneedling roller may be used with standardized razor blade cartridges or even, without the cartridge, separately from shaving.

A fifth aspect of the disclosure relates to a razor that may comprise a razor head according to any one of the first to fourth aspects, and a handle.

A sixth aspect of the disclosure relates to a method for cosmetic skin treatment using the razor head according to any one of the first to fourth aspects, including a microneedling step with the roller, wherein the microneedles penetrate under the stratum corneum, preferably without reaching the stratum basale. In particular, the method may also include a shaving step with the shaving blades before the microneedling step. Furthermore, the microneedles may inject a cosmetic skin care agent under the stratum corneum during the microneedling step.

The above summary of some example embodiments is not intended to describe each disclosed embodiment or every implementation of the disclosure. In particular, selected features of any illustrative embodiment within this specification may be incorporated into an additional embodiment unless clearly stated to the contrary.

BRIEF DESCRIPTION OF THE DRAWINGS

The invention may be more completely understood in consideration of the following detailed description of various embodiments in connection with the accompanying drawings, in which.

Figure 1:
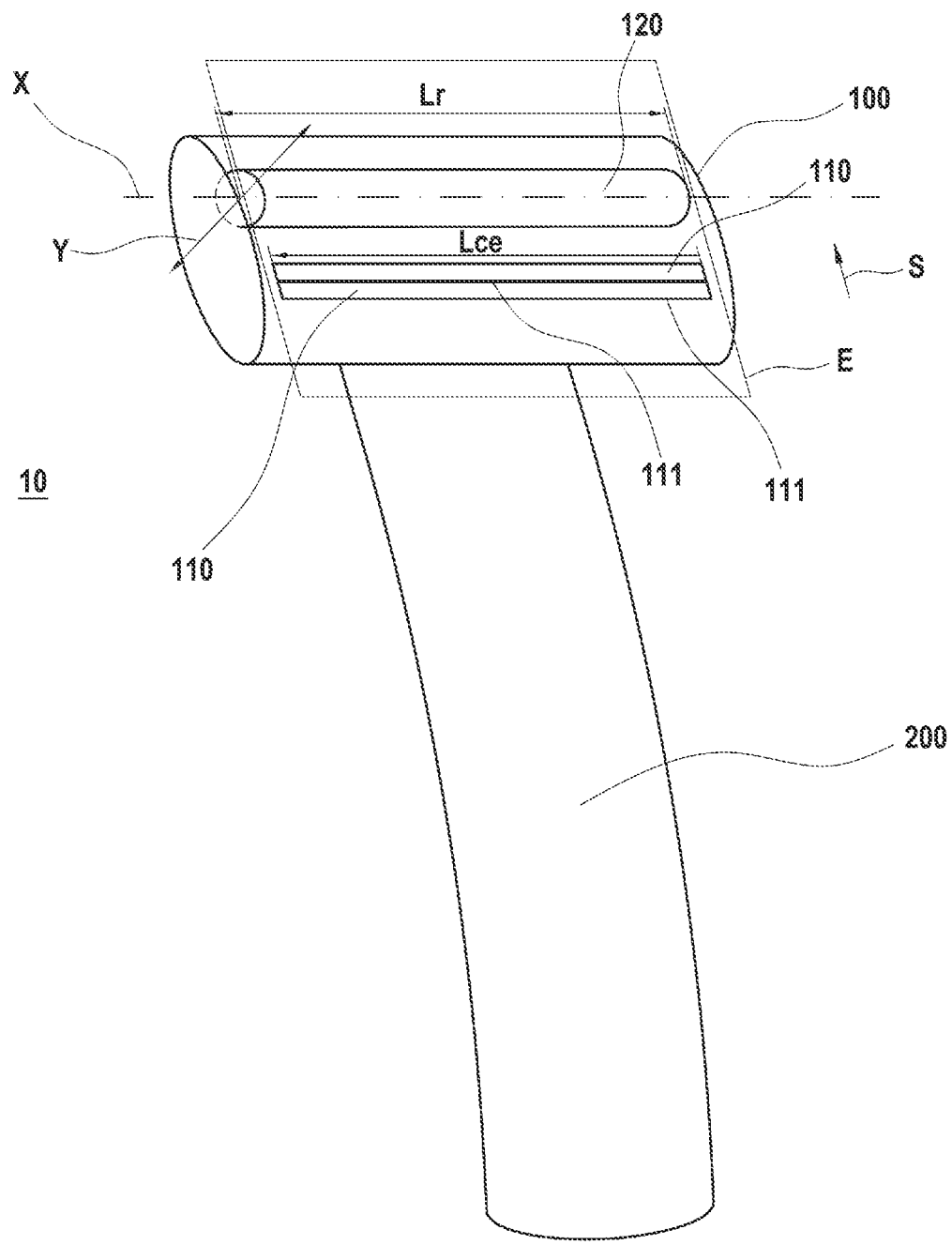
FIG. 1 is a schematic view of a razor with a razor head according to a first embodiment.

While the disclosure is amenable to various modifications and alternative forms, specifics thereof have been shown by way of example in the drawings and will be described in detail. It should be understood, however, that the intention is not to limit aspects of the disclosure to the particular embodiments described.

On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be preceded by the term "about", whether or not explicitly indicated. The term "about" generally refers to a range of numbers that one of skill in the art would consider equivalent to the recited value (i.e. having the same function or result). In many instances, the term "about" may be indicative as including numbers that are rounded to the nearest significant figure.

Any recitation of numerical ranges by endpoints includes all numbers within that range (e.g., 1 to 5 includes a.o. 1, 4/3, 1.5, 2, e, 2.75, 3, π, 3.80, 4, and 5).

Although some suitable dimension ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In embodiments, as shown in FIG. 1, a razor 10 may comprise a razor head 100 and a razor handle 200. The razor head 100 may comprise one or more shaving blades 110, which as shown may each have an exposed cutting edge 111 facing in a first direction S within a shaving plane E defined by the cutting edges 111. The cutting edges 111 may be substantially parallel to each other, and have each a length $L_{ce}$.

The razor head 100 may also comprise a roller 120. This roller 120 may be located behind at least one of the cutting edges 111 in said first direction S, and it may be held rotatable around a rotation axis X substantially parallel to the cutting edges 111. The roller 120 may have a length $L_r$, along said rotation axis X, at least equal to the length $L_{ce}$ of the cutting edges 111, and it may be substantially cylindrical.

Figure 4:
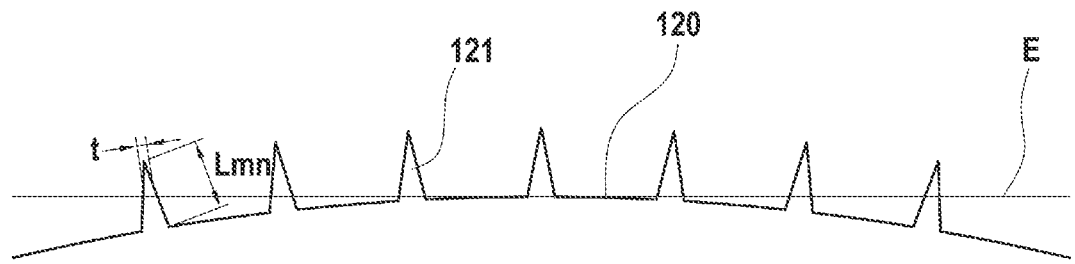
FIG. 4 is a detail view of a microneedling roller for any one of the razor heads of the first to third embodiments.

As shown in FIGS. 4, the roller 120 may comprise a plurality of outwardly extending microneedles 121. Each microneedle 121 may have a length $L_{mn}$ below 1.5 mm, more specifically below 1 mm, most specifically between 0.25 and 0.5 mm, and a tip thickness t below 100 μm, more specifically below 50 μm, most specifically between 1 and 25 μm. The rotation axis X of the roller 120 may be adjustable along another axis Y substantially orthogonal to the shaving plane E to adjust how far the microneedles 121 will protrude with respect of the shaving plane E. The microneedles 121 may be homogeneously distributed over an outer surface of the roller 120, for example with a surface density below 100 microneedles/mm², more specifically below 50 microneedles/mm², most specifically below 20 microneedles/mm². In examples, however, the microneedles 121 may be heterogeneously distributed over the outer surface of the roller 120, for example following a density gradient and/or a distribution pattern.

Figure 5A:
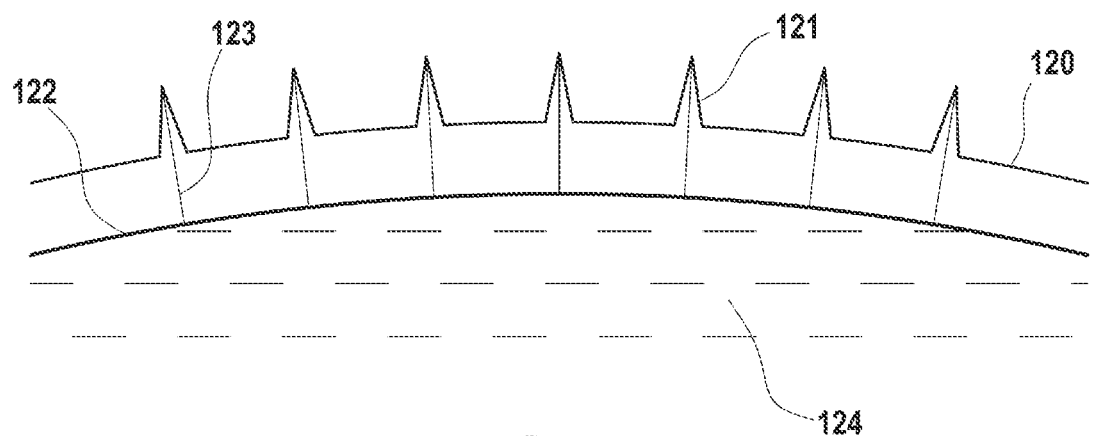
FIG. 5A is a detail view of an alternative microneedling roller for any one of the razor heads of the first to third embodiments.
Figure 5B:
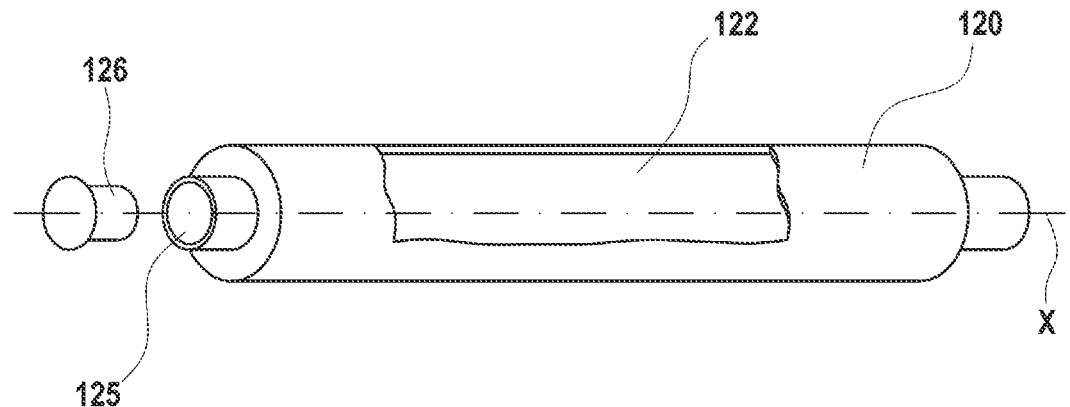
FIG. 5B is a schematic, general cutaway view of the microneedling roller of FIG. 5A.

In a first variant, as shown in FIG. 4, the microneedles 121 may be solid. However, alternatively to or in combination with these solid microneedles 121, the roller 120 may comprise hollow microneedles 121, open at their respective tips, for delivering a skin care agent, as in the second variant illustrated in FIGS. 5A and 5B. In this case, as shown in FIG. 5B, the roller 120 may also comprise an internal reservoir 122, in fluid communication with the hollow microneedles 121 through channels 123, for containing the skin care agent 124. The roller 120 may also comprise a sealable opening 125 for filling the reservoir 122 with the skin care agent 124. As shown, this opening 125 may be aligned with the rotation axis X, and the roller 120 may further comprise a plug 126 for sealing the opening 125.

The skin care agent 124 may in particular comprise a sun care, hydrating, antioxidant, or hair loss treatment agent. For example, the skin care agent 124 may comprise a mixture of hyaluronic acid and cerium-containing nanoparticles as a hair loss treatment agent, methylene blue as a comparatively eco-friendly sun care agent protecting against UV rays while also repairing UV-induced damage, or moringa oleifera seed oil as an antioxidant and hydrating agent.

Figure 2:
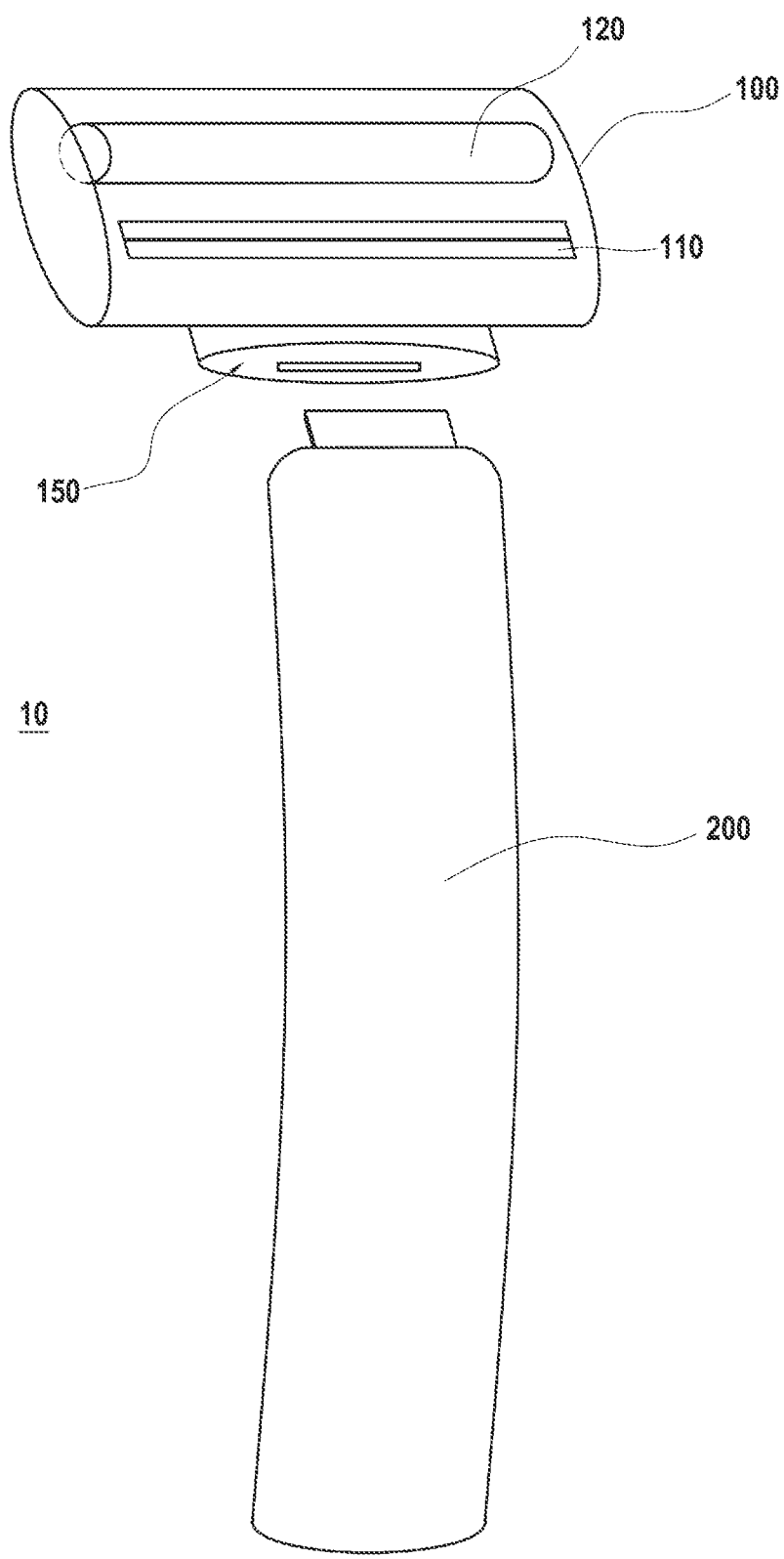
FIG. 2 is a schematic view of a razor with a razor head according to a second embodiment.
Figure 3:
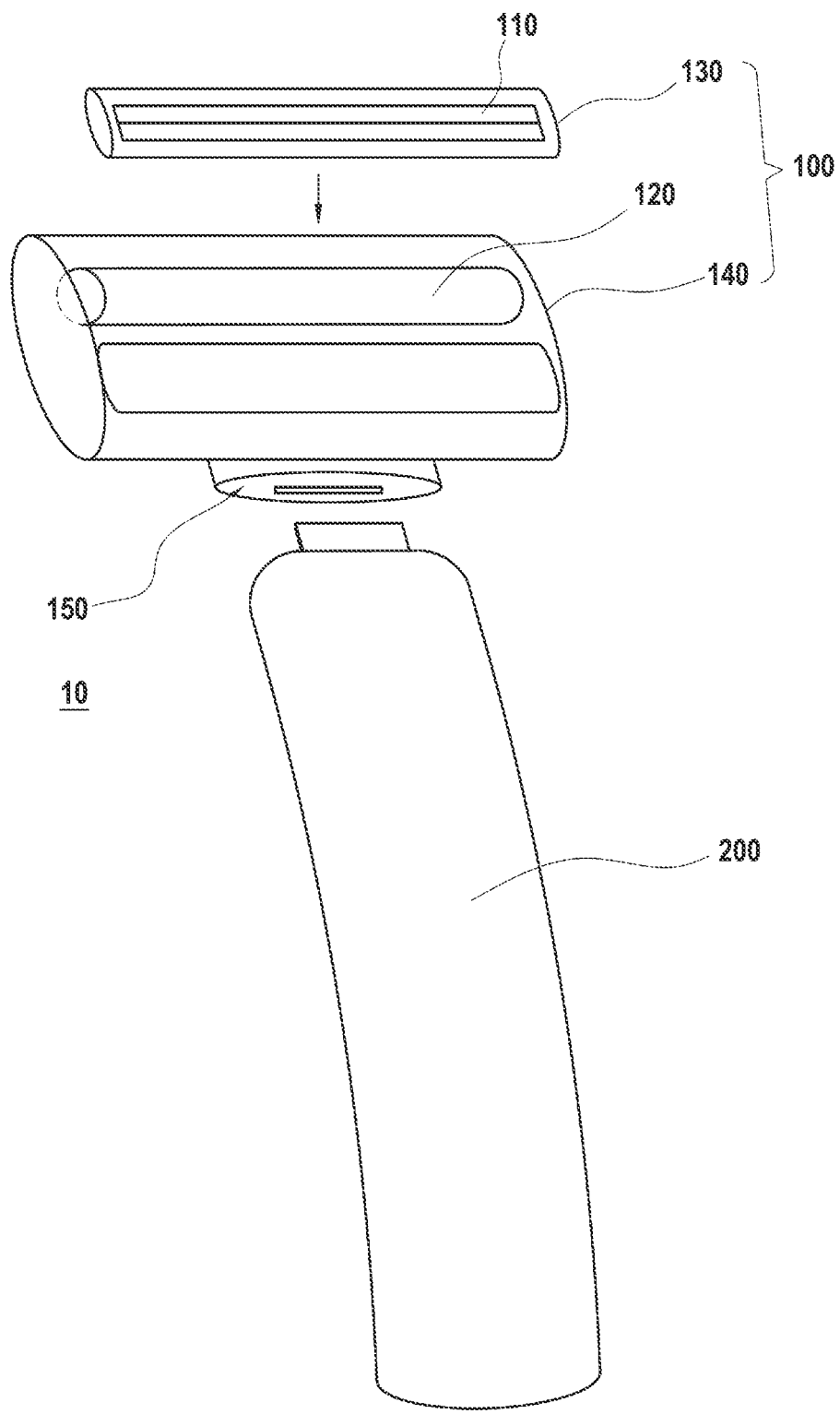
FIG. 3 is a schematic view of a razor with a razor head according to a third embodiment.

In embodiments, the razor 10 may be a disposable razor wherein at least part of the razor head 100 is integrally formed with the razor handle 200, as shown in FIG. 1. In examples, however, the razor 10 may have a releasable razor head 100 including both the shaving blades 110 and the roller 120, as in the embodiments respectively illustrated in FIGS. 2 and 3. In embodiments such as shown in FIG. 2, the shaving blades 110 and the roller 120 may both be held by a common razor head structure 130, directly connected to and releasable from the razor handle 200 through a connector 150. This releasable razor head 100 may thus be replaced, for example when the cutting edges 111 are blunted or the roller 120 runs out of skin care agent and is not refillable. In embodiments such as shown in FIG. 3, the razor head 100 may comprise a cartridge 130 comprising the shaving blades 110 and an adaptor 140 comprising the roller 120, wherein the cartridge 130 is releasable from the adaptor 140. The cartridge 130, may thus be replaced, for example when the cutting edges 111 are blunted, without necessarily replacing the adaptor 140 comprising the roller 120. The adaptor 140 may itself be releasably connected to the razor handle 200 through a connector 150, as illustrated, or alternatively it may be integrally formed with the razor handle 200. In either case, the adaptor 140 on the razor handle 200 may also be used without the cartridge 130, to perform microneedling dissociated from shaving. The remaining elements of the razors according to the embodiments as illustrated in FIGS. 2 and 3 may be as described for the embodiments as illustrated in FIG. 1 and accordingly receive the same reference numbers in those figures.

Figure 6:
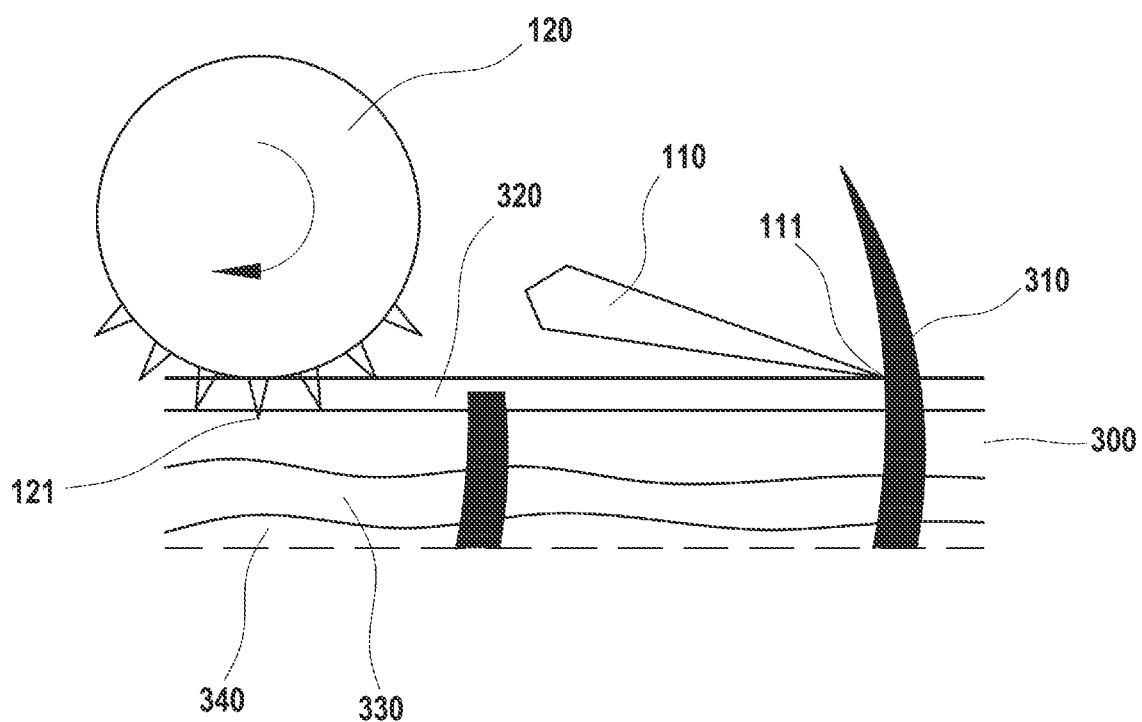
FIG. 6 is a schematic view of the concurrent shaving and microneedling actions of a razor head according to any one of the first to third embodiments.

Using the razor 10 according to any one of the above embodiments, the razor head 100 may glide over the user's skin 300, as illustrated on FIG. 6, with the shaving blades 110 cutting and pulling follicles 310 in a shaving step, while the microneedles 121 concurrently penetrate the stratum corneum 320, preferably without reaching the stratum basale 330 or the underlying dermis 340, as the roller 120 rolls on the shaven skin surface 350 trailing behind the shaving blades 110. When the microneedles 121 are hollow, as in the second variant illustrated on FIGS. 5A and 5B, they may then inject the drug or skin care agent 124 under the stratum corneum 320 or draw tissue and/or fluid samples from under the stratum corneum.

Those skilled in the art will recognize that the present invention may be manifested in a variety of forms other than the specific embodiments described and contemplated herein. Accordingly, departure in form and detail may be made without departing from the scope of the present invention as described in the appended claims.

The invention claimed is:

1. A razor head comprising one or more shaving blades and a roller, wherein the roller is adjacent to the shaving blades and includes a plurality of microneedles.

2. The razor head according to claim 1, wherein the microneedles are hollow.

3. The razor head according to claim 2, wherein the roller includes an internal reservoir, in fluid communication with the hollow microneedles.

4. The razor head according to claim 3, wherein the roller incudes a sealable opening.

5. The razor head according to claim 1, wherein the microneedles have a length below 1.5 mm.

6. The razor head according to claim 1, wherein the microneedles have a tip thickness below 100 µm.

7. The razor head according to claim 1, wherein a rotation axis (X) of the roller is substantially parallel to cutting edges of the shaving blades.

8. The razor head according to claim 1, wherein the microneedles are distributed with a surface density below 100 microneedles/mm$^2$ over an outer surface of the roller.

9. The razor head according to claim 7, wherein the roller is substantially cylindrical.

10. The razor head according to claim 7, wherein the roller has a length ($L_r$), along the rotation axis (X), at least equal to a length ($L_{ce}$) of each cutting edge of the shaving blades.

11. The razor head according to claim 1, comprising a releasable cartridge containing the shaving blades.

12. A razor comprising the razor head according to claim 1 and a handle.

13. A method for cosmetic skin treatment using the razor head according to claim 1, including a microneedling step with the roller, wherein the microneedles penetrate under the stratum corneum.

14. The method for cosmetic skin treatment according to claim 13, including a shaving step with the shaving blades before the microneedling step.

15. The method for cosmetic skin treatment according to claim 13, wherein the microneedles inject a cosmetic skin care agent under the stratum corneum during the microneedling step.

* * * * *